(12) United States Patent
Su et al.

(10) Patent No.: US 7,057,044 B2
(45) Date of Patent: Jun. 6, 2006

(54) APORPHINE AND OXOAPORPHINE COMPOUNDS AND PHARMACEUTICAL USE THEREOF

(75) Inventors: MingJai Su, Taipei (TW); ShoeiSheng Lee, Taipei (TW)

(73) Assignee: Lotus Pharmaceutical Co., Ltd., Taipei Taiwan ( * ) Notice: Subject to any disclaimer, the term of this patent is extended or adjusted under 35 U.S.C. 154(b) by 0 days.

(21) Appl. No.: 10/817,641

(22) Filed: Apr. 2, 2004

(65) Prior Publication Data

US 2004/0198759 A1 Oct. 7, 2004

(30) Foreign Application Priority Data

| Apr. 4, 2003 | (TW) | ................................ 92107780 A |
| Jun. 19, 2003 | (CN) | ................................ 03 1 37381 |
| Jun. 19, 2003 | (WO) | ...................... PCT/CN03/00477 |

(51) Int. Cl.
*C07D 221/18* (2006.01)

(52) U.S. Cl. ........................................ 546/75; 514/284
(58) Field of Classification Search ................ 546/75; 514/284

See application file for complete search history.

(56) References Cited

U.S. PATENT DOCUMENTS 5,156,847 A * 10/1992 Lewis et al. ................ 424/447

OTHER PUBLICATIONS

Khroyan, TV et al 'Dopamine D1- and D2- like receptor mechanisms in relapse to cocaine-seeking behavior: effects of selecti antagonists and agonists' J. of Pharmacology and Experimental Therapeutics (2000), 294(2), 680-687.*

Lan, YH et al 'Cytotoxic styrylpyrones from *Goniothalamus amuyon*' J. of Natural Products (2003), 66(4), 487-490.*

Zhang, CF et al 'Sesquiterpenes and alkaloids from *Lindera chunii* and their inhibitory activities against HIV-1 integrase' Chemical & Pharmaceutical Bulletin, (2002), 50(9), 1195-1200.*

Li-Man Hung, et al. "Thaliporphine Protects Ischemic and Ischemic-Reperfused Rat Hearts Via an NO-Dependent Mechanism" Drug Development Research 52:446-453 (2001).

* cited by examiner

Primary Examiner—Amelia A. Owens
(74) Attorney, Agent, or Firm—Osha Liang LLP

(57) ABSTRACT

The invention provides aporphine and oxoaporphine compounds that have endothelial nitric oxide synthase (eNOS) maintaining or enhancing activities and may be used to manufacture a medicaments for preventing or treating ischemic diseases in human and mammal, and the ischemic diseases may include ischemic cerebral apoplexy, ischemic cerebral thrombosis, ischemic cerebral embolism, hypoxic ischemic encephlopathy, ischemic cardiac disease or ischemic enteropathy etc.

3 Claims, 4 Drawing Sheets

APORPHINE AND OXOAPORPHINE COMPOUNDS AND PHARMACEUTICAL USE THEREOF

CROSS-REFERENCE TO RELATED APPLICATIONS

This application claims priority from Taiwanese Application No. TW92107780 filed on Apr. 4, 2003, Chinese Application No. 03137381.X filed on Jun. 19, 2003, and PCT Application No. PCT/CN03/00477 filed on Jun. 19, 2003.

BACKGROUND OF INVENTION

1. Field of the Invention

The present invention relates to compounds for treating ischemic diseases, more particularly to aporphine and oxoaporphine compounds that can be used to prevent or treat ischemic diseases based on a mechanism of maintaining or increasing the endothelial nitric oxide synthase (eNOS).

2. Background of the Invention

With the progress of society and the advance in sciences and technology, life expectancy gradually increases. Many people now suffer from various diseases due to old age, diet, obesity, lack of exercise or living under stress. Among these diseases, ischemic diseases are among the main causes of death and physical impairment. Ischemic diseases have a major impact and cause substantial loss to people, family, society and the state. Therefore, it is important to find agents to prevent the ischemic diseases.

Among various ischemic diseases, ischemic stroke has a high rate of morbidity, mortality, handicap and recurrence, and it is a common disease among middle-aged and old people. Occlusion of the extracranial or intracranial arteries, which supply blood to the brain, may cause brain ischemia and hypoxemia, resulting in a series of acute clinical symptoms (i.e. ischemic stroke). If blood supply cannot be restored in time, nerve cells, glial cells, vascular endothelial cell and smooth muscle cells will die, leading to cerebral infarction and cerebral thrombosis.

For the ischemic stroke, the thrombolytic agent, tissue plasminogen activator, is the only medicament that can re-open occluded blood vessels. Tissue plasminogen activator is also the only medicament that has been approved for treating thromboembolic stroke by the Food and Drug Administration in the U.S., and it was also approved by the Health Administration in Taiwan in 2001. However, because patients may suffer cerebral hemorrhagic complication after using a thrombolytic agent, this agent is strictly restricted in its use in a therapeutic window, i.e. "critical period." This drug should be injected intravenously within 3 hours after stroke, or injected intra-arterially with the aid of cerebral angiography to directly lyse the thrombus within 6 hours after stroke.

Other conventional blood vessel unblocking agents, such as anticoagulants and platelet aggregation inhibitors, can only prevent continued thrombus formation, but cannot lyse the thrombus to re-open occluded blood vessels. In addition, brain tissue protecting agents (such as Piracetam) also offer a promising therapy for thrombosis. However, these agents also need to be administrated within 6 hours after stroke to achieve a significant effect.

Recent studies show that blood clot dissolving agents can trigger the production and release of oxygen free radicals, platelet activating factor (PAF), and excitotoxic neurotransmitter, such as glutamate, which may act as N-methyl-D-aspartic acid (NMDA) to stimulate the NMDA receptor and consequently lead to neuronal cell death. Though MK801, an NMDA receptor antagonist, can reduce the injury (or infarction) in ischemia or ischemia-reperfusion brain tissue, the hypothermic effect, suppression of memory and other side effects of this agent prevent it from being used as a therapeutic agent.

SUMMARY OF THE INVENTION

One object of the invention is to provide aporphine and oxoaporphine compounds that can be used in the prevention and treatment of local ischemia. These compounds prevent and treat local ischemic injury by maintaining or increasing endothelial nitric oxide synthase (eNOS) activity.

Another finding of the present study is that aporphine and oxoaporphine compounds can dilate blood vessels and are more effective in opening up blocked vessels than conventional clot dissolving agents. As compared with MK801, these aporphine and oxoaporphine compounds will not cause memory loss or hypothermic side effects when they are used to treat ischemic diseases. Therefore, these compounds can provide better therapeutic index.

To achieve the above-described objectives, some embodiments of the present invention provide aporphine and oxoaporphine compounds for the prevention and treatment of local ischemic diseases, by maintaining or increasing endothelial nitric oxide synthetase (eNOS) activity. A composition of the invention includes an effective amount of a compound having the following structure I:

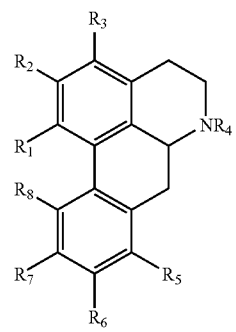

where $R_1$, $R_2$, $R_6$ and $R_7$ are each selected from H, OH, O-acyl, OMe, OEt, O"Pr and O$^i$Pr, $R_3$ and $R_5$ are each selected from H, OH, O-acyl, OMe, F, Cl, Br, $NH_2$, $NO_2$ and CN; $R_4$ is selected from allyl and $C_nH_{2n+1}$, $n \geq 0$; and $R_8$ is selected from H, OH, and OMe.

Some embodiments of the present invention provide aporphine and oxoaporphine compounds for the prevention and treatment of local ischemic diseases. These compounds function by maintaining or increasing endothelial nitric oxide synthetase (eNOS) activity. A composition of the invention includes an effective amount of a compound having the following structure II:

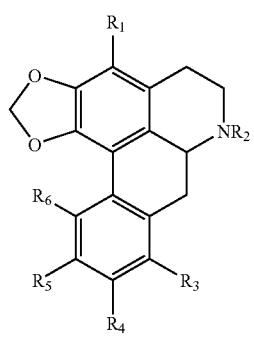

where R1 and $R_3$ are each selected from H, OH, O-acyl, OMe, F, Cl, Br, $NH_2$, $NO_2$ and CN; $R_2$ is selected from allyl and $C_nH_{2n+1}$, $n \geq 0$; $R_4$ and $R_5$ are each selected from H, OH, O-acyl, OMe, OEt, O"Pr, and O$^i$Pr; and $R_6$ is selected from H, OH, O-acyl, and OMe.

Some embodiments of the present invention provide aporphine and oxoaporphine compounds for the prevention and treatment of local ischemic diseases. These compounds function by maintaining or increasing endothelial nitric oxide synthetase (eNOS) activity. A composition of the invention includes an effective amount of a compound having the following structure III:

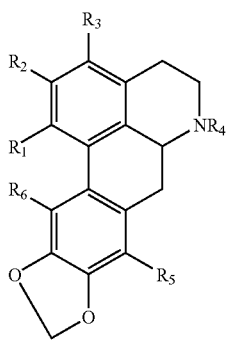

III where $R_1$ and $R_2$ are each selected from H, OH, O-acyl, OMe, OEt, O"Pr, and O$^i$Pr; $R_3$ and $R_5$ are each selected from H, OH, O-acyl, OMe, F, Cl, Br, $NH_2$, $NO_2$ and CN; $R_4$ is selected from allyl and $C_nH_{2n+1}$, $n \geq 0$; and $R_6$ is selected from H, OH, O-acyl, and OMe.

Some embodiments of the present invention provide aporphine and oxoaporphine compounds for the prevention and treatment of local ischemic diseases. These compounds function by maintaining or increasing endothelial nitric oxide synthetase (eNOS) activity. A composition of the invention includes an effective amount of a compound having the following structure IV:

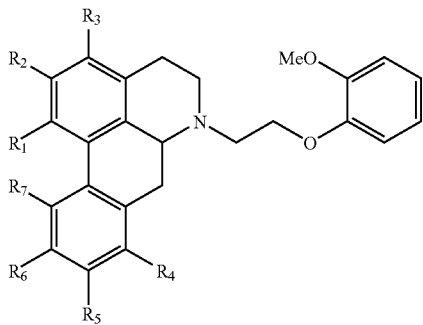

IV where $R_1$, $R_2$, $R_5$ and $R_6$ are each selected from H, OH, O-acyl, OMe, OEt, O"Pr, and O$^i$Pr; $R_3$ and $R^4$ are each selected from H, OH, O-acyl, OMe, F, Cl, Br, $NH_2$, $NO_2$ and CN; and $R_7$ is selected from H, OH, O-acyl, and OMe.

Some embodiments of the present invention provide aporphine and oxoaporphine compounds for the prevention and treatment of local ischemic diseases. These compounds function by maintaining or increasing endothelial nitric oxide synthetase (eNOS) activity. A composition of the invention includes an effective amount of a compound having the following structure V:

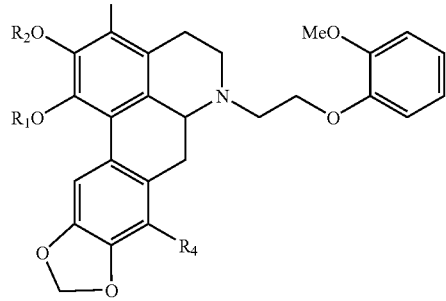

V where $R_1$ and $R_2$ are each selected from H, acyl, Me, Et, "Pr, and $^i$Pr; $R_3$ and $R_4$ are each selected from H, OH, O-acyl, OMe, F, Cl, Br, $NH_2$, $NO_2$ and CN.

Some embodiments of the present invention provide an aporphine and oxoaporphine compounds for the prevention and treatment of local ischemic diseases. These compounds function by maintaining or increasing endothelial nitric oxide synthetase (eNOS) activity. A composition of the invention includes an effective amount of a compound having the following structure VI:

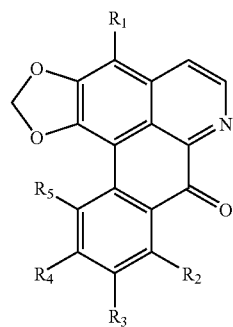

VI where $R_1$ and $R_2$ are each selected from H, OH, O-acyl, OMe, F, Cl, Br, $NO_2$ and CN; $R_3$ and $R_4$ are each selected from H, OH, O-acyl, OMe, OEt, O"Pr, and O$^i$Pr; and $R_5$ is selected from H, OH, O-acyl, and OMe.

Some embodiments of the present invention provide aporphine and oxoaporphine compounds for the prevention and treatment of local ischemic diseases. These compounds function by maintaining or increasing endothelial nitric oxide synthetase (eNOS) activity. A composition of the invention includes an effective amount of a compound having the following structure VII:

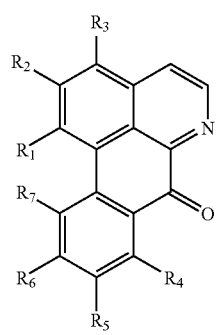

VII where $R_1$, $R_2$, $R_5$ and $R_6$ are each selected from H, OH, O-acyl, OMe, OEt, O"Pr and O'Pr; $R_3$ and $R_4$ are each selected from H, OH, O-acyl, OMe, F, Cl, Br, $NO_2$ and CN; and $R_7$ is selected from H, OH, O-acyl, and OMe.

Some embodiments of the present invention provide aporphine and oxoaporphine compounds for the prevention and treatment of local ischemic diseases. These compounds function by maintaining or increasing endothelial nitric oxide synthetase (eNOS) activity. A composition of the invention includes an effective amount of a compound having the following structure VIII:

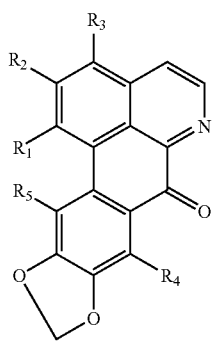

VIII where $R_1$ and $R_2$ are each selected from H, OH, O-acyl, OMe, OEt, O"Pr and O'Pr; $R_3$, and $R_4$ are each selected from H, OH, O-acyl, OMe, F, Cl, Br, $NO_2$ and CN; and $R_5$ is selected from H, OH, O-acyl, and OMe.

These compounds can be used in the manufacture of medicaments for treating ischemic diseases in mammal or human beings. The ischemic diseases include ischemic cerebral apoplexy, ischemic cerebral thrombosis, ischemic cerebral embolism, hypoxia and ischemic encephlopathy, ischemic cardiac disease, ischemic enteropathy, and the like.

Compared with the current methods for lysing the infarcted thrombus to open up blood vessels, the compounds of the invention have better therapeutic efficacies by loosening and dilating the blood vessels. There are little side effects in treating the ischemic diseases with the aporphine and oxoaporphine compounds of the invention. These side effects may include, for example, s memory loss, body temperature decreasing.

The present invention also discloses the use of aporphine or oxoaporphine compounds in the prophylaxis or treatment of ischemic diseases, and further discloses the use of aporphine and oxoaporphine compounds in the prophylaxis or treatment of ischemic diseases in mammal and human beings.

The invention also provides pharmaceutical compositions for the prophylaxis or treatment of ischemic diseases. A pharmaceutical composition in accordance with embodiments of the invention comprises a therapeutically effective amount of aporphine or oxoaporphine compounds and a pharmaceutically acceptable carrier or excipient. One of ordinary skill in the art would appreciate that "an effective amount" refers to an amount sufficient to achieve the prevention or treatment of an ischemic disease. The specific amount will depend on the age, body weight of the patient and the specific ischemia.

The following examples and the associated figures further describe and demonstrate embodiments of the present invention. These examples are given solely for illustration and are not intended to limit the scope of the invention to these illustrated examples.

DETAILED DESCRIPTION OF THE INVENTION

Figure 1:
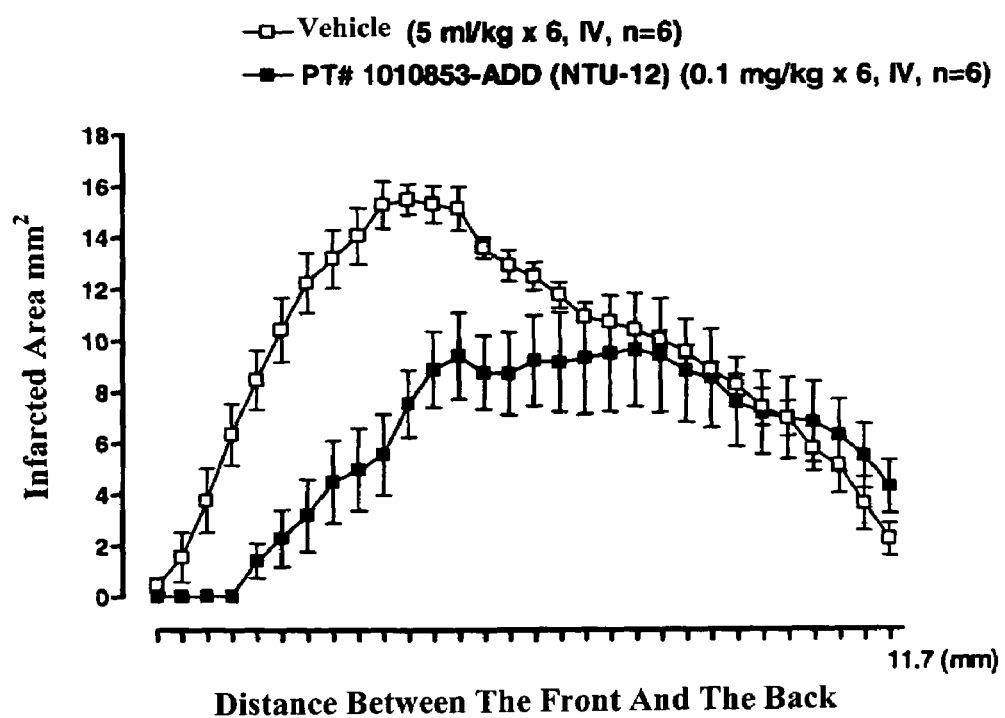
FIG. 1 shows the results of groups I and II in the pharmacodynamic study using a compound in accordance with one embodiment of the invention.

Human blood vessels can synthesize nitric oxide (NO). NO can dilate blood vessels and, therefore, NO production is closely associated with blood pressure regulation. Endogenous NO plays an important role in the vascular smooth muscle relaxation. In ex vivo experiments using an isolated aortic ring and local blood vessel layer and in vivo whole body experiments have shown that the blood vessels constrict and the blood pressures elevate upon the interruption of NO formation. In mammals, NO is synthesized from L-arginine by nitric oxide synthase (NOS). The NOS converts L-arginine to an intermediate, which is then converted to L-citrulline and NO as follows:

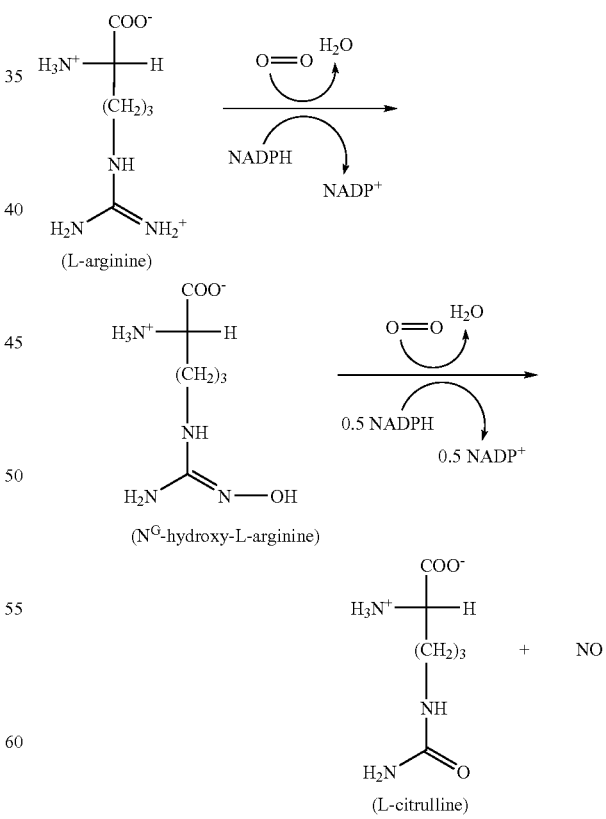

NOS exists in at least three isoforms, including neuronal NOS (NOS, or type I NOS), inducible NOS (iNOS, or type II NOS), and endothelial NOS (eNOS, or type III NOS).

Among these, the function of eNOS is responsible for the regulation of blood vessel tension. The function and mechanism of NO as a signal transduction messenger vary depending on where it is produced. eNOS has three major functions: (1) in nerve synapse, it produces NO as nerve in pulse conduction factor and it may contribute to brain learning and memory; (2) in blood vessel endothelia, it produces NO to relax vascular smooth muscle so as to dilate the vessel and lower blood pressure; and (3) in macrophage, it produces NO to destroy and kill tumor cells to prevent their growth.

nNOS and eNOS are complex enzymes, requiring calcium and calmodulin. Calcium first binds to calmodulin, then the calcium-calmodulin complex binds nNOS or eNOS to activate its catalytic activity. On the other hand, iNOS is inducible and does not depend on calcium or calmodulin. Instead, iNOS is induced by cytokines. Because iNOS is calcium-independent and calmodulin-independent, the activity of iNOS once induced cannot be easily terminated and may last for several hours, leading to overproduction of NO, which can be harmful.

Prior to the present invention, research on compounds that can maintain or increase eNOS activities is mostly focused on the treatment of cardiovascular diseases (e.g., arrhythmia, Su M J, et al., Drug Development Research, 2001, 52:446–453). The present invention provides new compounds that function by a similar mechanism but can be used to prevent or treat ischemic diseases, such as stroke. The following describes methods and results of using these compounds in the treatment of ischemic diseases.

The invention relates to aporphine and oxoaporphine compounds for use in preventing or treating ischemic diseases. These compounds function by maintaining or increasing endothelial nitric oxide synthase (eNOS) activities. One example of these compounds is Liriodenine, which is one of the formula VI compounds, where R1 through R5 are H. Liriodenine is used as a preferred example to demonstrate the present invention. The structure of Liriodenine, which is a plant alkaloid, is as follow:

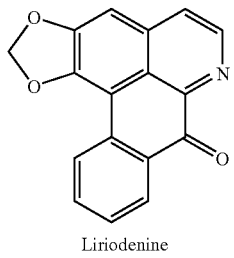

Liriodenine

After Liriodenine was administrated to male Sprague Dawley rats, the effects of Liriodenine on the artery occlusive cerebral ischemia in the rats were monitored. First, permanent brain ischemia was induced by middle cerebral artery occlusion (MCAO) in the rats. At 0, 6, 24, 48, and 54 hours after the formation of middle cerebral artery occlusion (MCAO), Group I (i.e., the control group) animals were given the solvent (0.9% NaCl) (5 ml/kg, i.v.); Group II animals (PT#1010853-ADD(NTU-12)(NTU-106)) were given Liriodenine (0.1 mg/kg, i.v.); Group III animals were given MK-801 (0.1 mg/kg, i.v.), an antagonist of the N-methyl-D-aspartic acid (NMDA) receptor. There were six rats in each group. The body temperature of each animal was measured anally before and 15 min after the administration of each treatment. Four days after the formation of MCAO, all the rats were sacrificed. Brain sections were made and stained with 2% cresol purple. The areas and volumes of cerebral ischemia lesions in each section were recorded.

Figure 2:
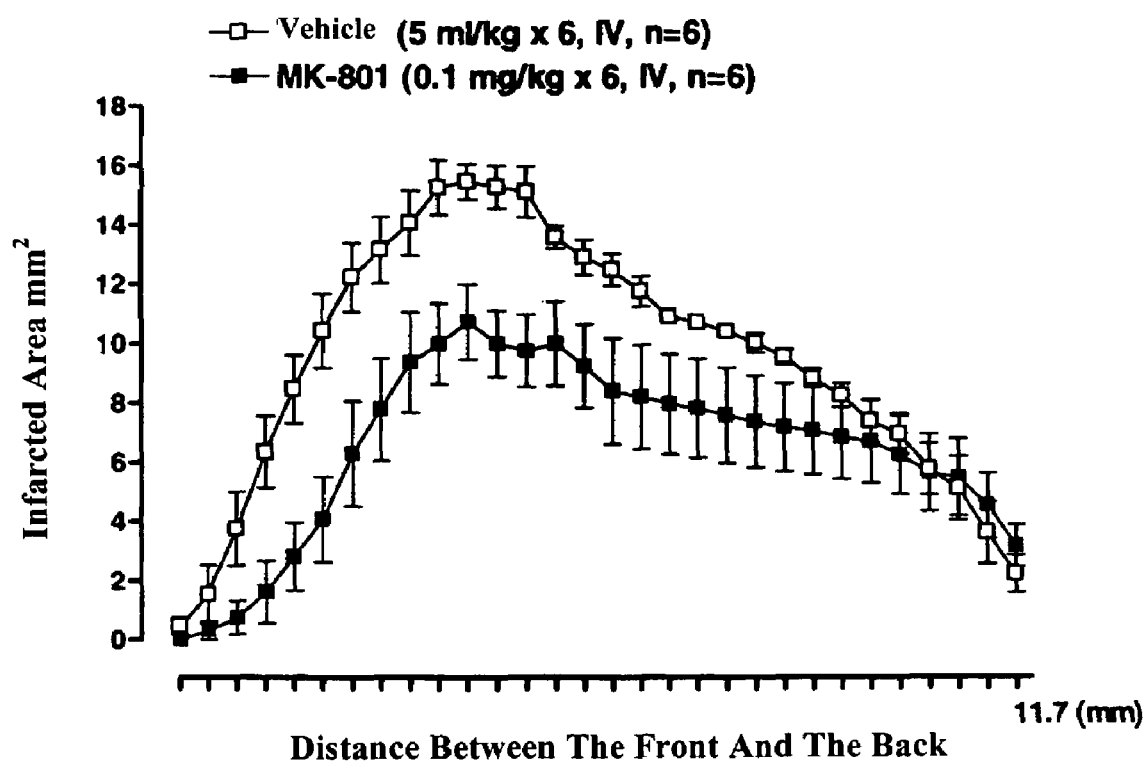
FIG. 2 shows the comparative curve of the results of group I and III in the pharmacodynamic study using a compound in accordance with one embodiment of the invention.

The results are shown in Table 1, 2 and 3, for Groups I, II, and III, respectively. The comparative results among these three groups are shown in Table 4. The results may also be shown as graphs. For example, FIG. 1 shows the comparative curves of the results of group I and group II, and FIG. 2 shows the comparative curves of the results of group I and group III. From these Tables and Figures, as compared with MK-801, it is apparent that the test compound Liriodenine had more significant effects in reducing the areas and volumes of cerebral ischemia lesions in the treatment of ischemic apoplexy. The results of the body temperature measurements are shown in Tables 5, 6 and 7 for Groups I, II, and III, respectively. Compared with the results of group I, the test compound Liriodenine did not cause significant changes in body temperatures, while MK-801 caused significant side effects, i.e. decreasing body temperatures.

Figure 3:
FIG. 3 shows effects of Liriodenine on eNOS protein and α-tubulin expression in a rat heart that had suffered ischemia for 30 min and was then reperfused for 2-hr.
Figure 4:
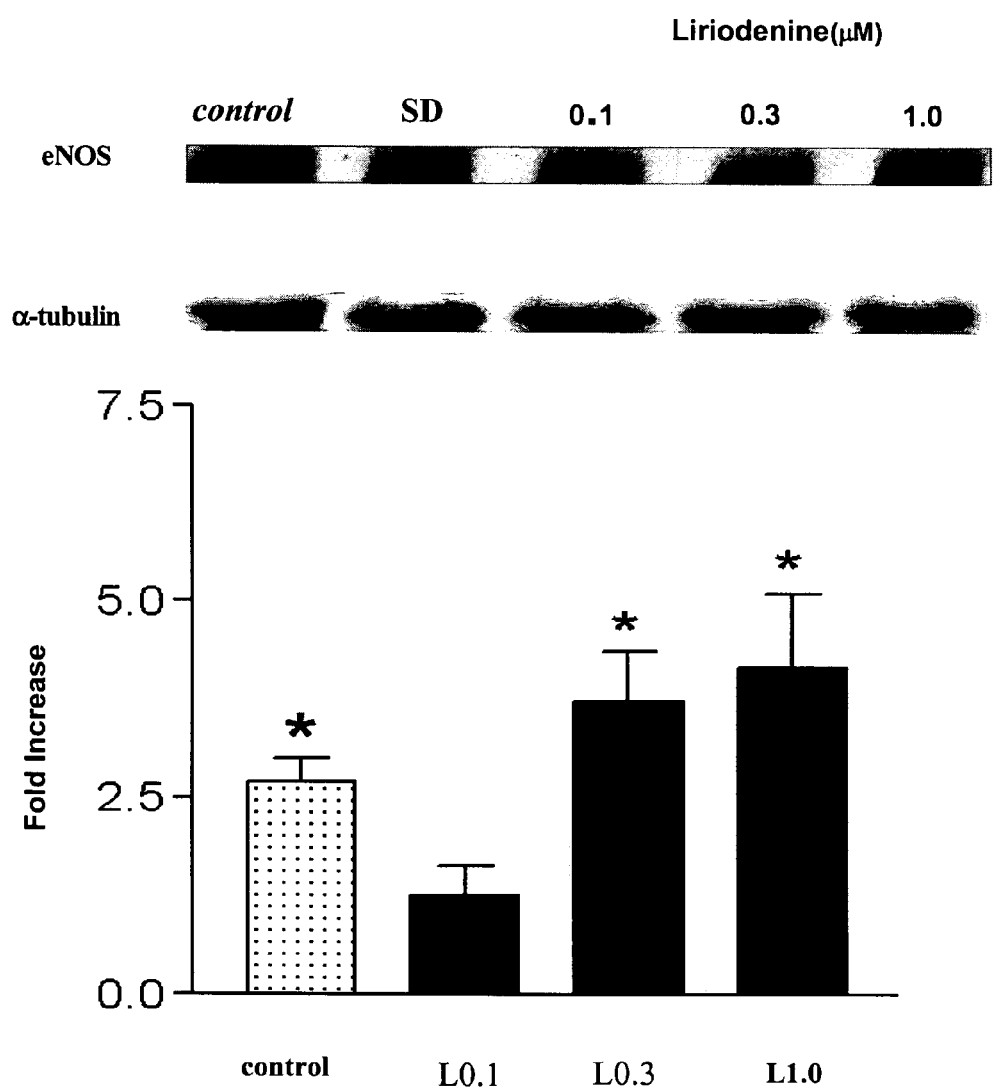
FIG. 4 shows effects of Liriodenine on eNOS protein expression in human being umbilical cord vessel endothelium cells (HUVEC).

FIG. 3 and FIG. 4 show that Liriodenine could protect eNOS or stimulate its production in ischemia-reperfusion heart and serum-deprived HUVECs (human umbilical vein endothelial cells) to achieve the aim of preventing or treating ischemic disease.

FIG. 3 shows the effects of Liriodenine on eNOS protein expression in a rat heart that had suffered ischemia for 30 min and then was reperfused for 2-hrs. The expression of α-tubulin was used as a quantitative control. In FIG. 3, lane a shows the effects on eNOS and α-tubulin expression in the hearts of male rats under normal conditions. Lane b shows the effects on eNOS and α-tubulin expression in the non-infarcted areas, wherein the left anterior descending branch coronary artery (LAD) of the heart had been ligated and then reperfused with a vehicle-containing solution. Lane c shows the effect on eNOS and α-tubulin expression in infarcted areas, wherein the left anterior descending branch coronary artery of the heart had been ligated and then reperfused with a vehicle-containing solution. Lane d shows the effects on eNOS and α-tubulin expression in non-infarcted areas, wherein the heart was pretreated with 1 μM Liriodenine and then the left anterior descending branch coronary artery of the heart was ligated and then reperfused with 1 μM Liriodenine. Lane e shows the effects on eNOS and α-tubulin expression in infarcted areas, wherein the heart was pretreated with 1 μM Liriodenine and then the left anterior descending branch coronary artery of the heart was ligated and then reperfused with 1 μM Liriodenine. From the difference in expression between eNOS and α-tubulin, it is clear that the expression of eNOS in the heart can approach the normal value after treatment with Liriodenine solution. These results show that a compound of the present invention (such as Liriodenine) can improve the expression of eNOS or maintain its expression at a constant level.

FIG. 4 shows the effects of Liriodenine on eNOS protein expression in human umbilical vein endothelium cells (HUVEC). As shown in this figure, eNOS protein level was significantly reduced under serum-deprived (SD) condition for 24 hours. Administrating Liriodenine from 0.1 to 1 μM can increase eNOS protein levels in serum-deprived HUVECs in a dose-dependent manner. The levels of eNOS protein expression are quantified using densitometer software, relative to the level of eNOS protein expression under the SD condition, which is set as 1 in the histogram. The results shown in the FIG. 4 are representative of three independent tests. Asterisks in the histogram indicate that the results have P<0.05, meaning the difference is significant from the level of HUVEC eNOS under SD. From the results in FIG. 4, it is clear that expression levels of eNOS increase significantly after the HUEVC was treated with 0.3 and 1 µM of Liriodenine. This result shows that Liriodenine is capable of maintaining eNOS expression level or enhancing the formation of eNOS.

Therefore, a composition of the invention can maintain the endothelial function by increasing eNOS activity. The functions of eNOS include inhibiting leukocyte and platelet adhesion, as well as regulating blood flow to organs etc. The functions of various forms of NOS on the cerebral ischemia are confirmed in a transgenic animal model. In local cerebral ischemia, the infarction is more severe in the eNOS gene-knockout mice than in the wild-type mice. In contrast, iNOS knockout mice or nNOS knockout mice have less infraction in local cerebral ischemia than the wild-type mice.

Results form the above test show that the compounds of the invention can decrease the volume and area of cerebral infarct in rats without the side effects caused by MK801 (an NMDA receptor antagonist).

In addition, the compound described above can treat ischemic diseases not only in rats, but also in the mammals and human being. The ischemic diseases include ischemic cerebral thrombosis, ischemic cerebral embolism, hypoxic ischemic encephlopathy, ischemic cardiac disease or ischemic enteropathy, as well as ischemic cerebral apoplexy.

TABLE 1

(Summary)
Calculated Decrease in Total Volume of Ischemic Lesions in the Brains of MCAO Rats by the Test Compound

| Treatment | Route | Dose | N | Infarcted Volume (X ±SEM mm$^3$) | % Decrease. (X ±SEM) |
|---|---|---|---|---|---|
| Vehicle Control | i.v. | 5 ml/kg × 6 | 6 | 109.92 ± 2.96 | — |
| PT #1010853-ADD (NTU-12) (NTU-106) | i.v. | 0.1 mg/kg × 6 | 6 | 71.37 ± 11.87* | 35.07 ± 10.80 |
| MK-801 | i.v. | 0.1 mg/kg × 6 | 6 | 75.17 ± 13.74* | 31.61 ± 12.50 |

*$P < 0.05$

TABLE 2

Area of Ischemic Lesions in Vehicle Control (0.9% NaCl, 5 ml/kg × 6, i.v.) MCAO Rats Infarcted Area (mm$^2$) of Each Test Animal

| Slice # | 1 | 2 | 3 | 4 | 5 | 6 | X ±SEM |
|---|---|---|---|---|---|---|---|
| BW (g) | 250 | 240 | 240 | 250 | 260 | 270 | N = 6 |
| 1 | 1.52 | 0 | 0 | 0 | 1.20 | 0 | 0.45 ± 0.29 |
| 2 | 5.05 | 0 | 0 | 0 | 4.20 | 0 | 1.54 ± 0.98 |
| 3 | 8.50 | 1.18 | 3.16 | 0 | 5.11 | 4.57 | 3.75 ± 1.24 |
| 4 | 10.80 | 4.50 | 4.62 | 2.68 | 8.25 | 7.17 | 6.34 ± 1.21 |
| 5 | 12.60 | 8.71 | 6.25 | 4.44 | 9.45 | 9.28 | 8.45 ± 1.15 |
| 6 | 15.00 | 9.38 | 8.68 | 6.49 | 13.00 | 9.97 | 10.42 ± 1.26 |
| 7 | 15.90 | 11.00 | 9.67 | 9.23 | 15.30 | 12.30 | 12.23 ± 1.15 |
| 8 | 16.00 | 12.00 | 10.80 | 10.30 | 16.90 | 13.00 | 13.17 ± 1.11 |
| 9 | 17.00 | 12.70 | 11.50 | 12.20 | 17.90 | 13.10 | 14.07 ± 1.10 |
| 10 | 17.60 | 14.20 | 11.60 | 15.30 | 17.60 | 15.30 | 15.27 ± 0.92 |
| 11 | 16.60 | 15.60 | 12.70 | 15.70 | 16.60 | 15.60 | 15.47 ± 0.59 |
| 12 | 15.80 | 13.70 | 12.80 | 15.80 | 15.90 | 17.70 | 15.28 ± 0.72 |
| 13 | 13.50 | 13.60 | 13.00 | 16.80 | 15.70 | 18.10 | 15.12 ± 0.85 |
| 14 | 13.30 | 12.60 | 12.70 | 14.80 | 13.40 | 14.70 | 13.58 ± 0.39 |
| 15 | 11.60 | 11.70 | 11.70 | 14.40 | 13.30 | 14.70 | 12.90 ± 0.58 |
| 16 | 11.50 | 11.10 | 11.50 | 14.20 | 12.70 | 13.90 | 12.48 ± 0.54 |
| 17 | 11.20 | 11.00 | 11.30 | 14.10 | 12.20 | 10.80 | 11.77 ± 0.51 |
| 18 | 10.00 | 10.90 | 11.20 | 11.80 | 10.70 | 10.80 | 10.90 ± 0.24 |
| 19 | 9.97 | 10.80 | 11.10 | 11.50 | 10.50 | 10.40 | 10.71 ± 0.22 |
| 20 | 9.96 | 10.70 | 11.00 | 11.00 | 9.82 | 9.90 | 10.40 ± 0.23 |
| 21 | 9.70 | 10.60 | 10.30 | 11.00 | 8.73 | 9.80 | 10.02 ± 0.33 |
| 22 | 9.60 | 9.72 | 9.76 | 10.50 | 8.68 | 8.97 | 9.54 ± 0.26 |
| 23 | 8.77 | 8.80 | 9.50 | 9.60 | 7.47 | 8.75 | 8.81 ± 0.31 |
| 24 | 8.74 | 8.44 | 8.74 | 8.86 | 6.30 | 8.35 | 8.24 ± 0.40 |
| 25 | 8.38 | 8.31 | 7.83 | 8.60 | 3.95 | 7.10 | 7.36 ± 0.72 |
| 26 | 7.96 | 7.73 | 7.12 | 8.38 | 3.82 | 6.55 | 6.93 ± 0.67 |
| 27 | 5.81 | 7.70 | 6.82 | 6.45 | 1.59 | 6.06 | 5.74 ± 0.87 |
| 28 | 5.73 | 7.41 | 6.62 | 5.87 | 0 | 4.96 | 5.10 ± 1.07 |
| 29 | 5.00 | 6.71 | 4.95 | 4.00 | 0 | 0.94 | 3.60 ± 1.06 |
| 30 | 3.09 | 2.61 | 3.83 | 3.11 | 0 | 0.58 | 2.20 ± 0.63 |
| Total mm$^2$ | 316.18 | 273.40 | 260.75 | 277.11 | 280.27 | 283.35 | 281.84 ± 7.58 |
| Total mm$^3$ | 123.31 | 106.63 | 101.69 | 108.07 | 109.31 | 110.51 | 109.92 ± 2.96 |

TABLE 3

Area of Ischemic Lesions in PT #1010853-ADD (NTU-12) (NTU-106)
(0.1 mg/kg × 6, i.v.) MCAO Rats Infarcted Area (mm$^2$) of Each Test Animal

| Slice # | 1 | 2 | 3 | 4 | 5 | 6 | X ±SEM |
|---|---|---|---|---|---|---|---|
| BW (g) | 230 | 240 | 240 | 250 | 240 | 230 | N = 6 |
| 1 | 0 | 0 | 0 | 0 | 0 | 0 | 0 |
| 2 | 0 | 0 | 0 | 0 | 0 | 0 | 0 |
| 3 | 0 | 0 | 0 | 0 | 0 | 0 | 0 |
| 4 | 0 | 0 | 0 | 0 | 0 | 0 | 0 |
| 5 | 0 | 3.86 | 2.61 | 0 | 0 | 1.97 | 1.41 ± 0.68 |
| 6 | 0 | 6.38 | 4.31 | 0 | 0 | 2.95 | 2.27 ± 1.11 |
| 7 | 0.93 | 8.47 | 5.33 | 0 | 0 | 4.30 | 3.17 ± 1.40 |
| 8 | 3.20 | 8.55 | 6.94 | 0 | 0 | 8.17 | 4.48 ± 1.61 |
| 9 | 4.52 | 9.10 | 7.91 | 0 | 0.61 | 7.68 | 4.97 ± 1.60 |
| 10 | 4.73 | 9.11 | 9.92 | 0 | 2.44 | 7.10 | 5.55 ± 1.58 |
| 11 | 8.54 | 10.30 | 10.50 | 1.75 | 6.97 | 7.09 | 7.53 ± 1.31 |
| 12 | 9.95 | 12.60 | 10.90 | 2.80 | 10.70 | 6.22 | 8.86 ± 1.49 |
| 13 | 10.60 | 12.00 | 13.80 | 3.44 | 11.30 | 5.23 | 9.39 ± 1.67 |
| 14 | 10.70 | 11.20 | 10.71 | 3.56 | 11.40 | 4.93 | 8.75 ± 1.44 |
| 15 | 11.50 | 10.70 | 9.99 | 3.84 | 12.54 | 3.67 | 8.71 ± 1.60 |
| 16 | 12.10 | 10.60 | 9.83 | 5.92 | 14.30 | 2.48 | 9.20 ± 1.76 |
| 17 | 12.40 | 10.50 | 9.70 | 6.59 | 14.50 | 1.17 | 9.14 ± 1.93 |
| 18 | 13.30 | 10.40 | 9.68 | 7.33 | 15.10 | 0 | 9.30 ± 2.17 |
| 19 | 13.90 | 10.40 | 9.55 | 7.37 | 15.70 | 0 | 9.49 ± 2.26 |
| 20 | 14.80 | 9.91 | 9.10 | 9.30 | 14.60 | 0 | 9.62 ± 2.20 |
| 21 | 15.20 | 9.31 | 9.08 | 8.56 | 14.29 | 0 | 9.41 ± 2.21 |
| 22 | 14.20 | 9.14 | 8.92 | 8.13 | 12.50 | 0 | 8.82 ± 2.01 |
| 23 | 13.90 | 9.01 | 8.85 | 7.79 | 11.44 | 0 | 8.50 ± 1.92 |
| 24 | 12.10 | 7.90 | 6.89 | 7.45 | 11.10 | 0 | 7.57 ± 1.74 |
| 25 | 10.50 | 7.86 | 6.71 | 6.76 | 11.00 | 0 | 7.14 ± 1.61 |
| 26 | 10.40 | 7.80 | 6.50 | 6.23 | 10.70 | 0 | 6.94 ± 1.59 |
| 27 | 10.30 | 7.68 | 6.05 | 6.16 | 10.60 | 0 | 6.80 ± 1.58 |
| 28 | 9.74 | 6.98 | 5.48 | 6.08 | 9.27 | 0 | 6.26 ± 1.43 |
| 29 | 8.03 | 5.88 | 4.80 | 5.35 | 8.79 | 0 | 5.47 ± 1.27 |
| 30 | 7.94 | 4.30 | 4.40 | 3.95 | 4.98 | 0 | 4.26 ± 1.04 |
| Total mm$^2$ | 243.48 | 229.94 | 208.46 | 118.36 | 234.83 | 62.96 | 183.00 ± 30.43 |
| Total mm$^3$ | 94.96 | 89.68 | 81.30 | 46.16 | 91.58 | 24.55 | 71.37 ± 11.87* |
| % Inh | 13.61 | 18.41 | 26.04 | 58.01 | 16.68 | 77.67 | 35.07 ± 10.80 |

TABLE 4

Area of Ischemic Lesions in MK-801
(0.1 mg/kg × 6, i.v.) MCAO Rats

Infarcted Area (mm$^2$) of Each Test Animal

| Slice # | 1 | 2 | 3 | 4 | 5 | 6 | X ±SEM |
|---|---|---|---|---|---|---|---|
| BW (g) | 220 | 250 | 250 | 260 | 240 | 270 | N = 6 |
| 1 | 0 | 0 | 0 | 0 | 0 | 0 | 0 |
| 2 | 0 | 1.91 | 0 | 0 | 0 | 0 | 0.32 ± 0.32 |
| 3 | 0 | 3.53 | 0 | 0 | 0 | 0.97 | 0.75 ± 0.58 |
| 4 | 0 | 5.86 | 0 | 0 | 0 | 3.76 | 1.60 ± 1.05 |
| 5 | 1.99 | 6.74 | 0 | 0 | 2.52 | 5.58 | 2.81 ± 1.15 |
| 6 | 4.33 | 8.02 | 0 | 0 | 4.32 | 7.78 | 4.08 ± 1.44 |
| 7 | 5.86 | 10.50 | 2.74 | 0 | 7.54 | 11.10 | 6.29 ± 1.78 |
| 8 | 6.97 | 11.90 | 5.11 | 1.18 | 9.83 | 11.70 | 7.78 ± 1.71 |
| 9 | 8.63 | 12.30 | 6.39 | 2.98 | 13.90 | 12.00 | 9.37 ± 1.70 |
| 10 | 10.60 | 12.80 | 7.72 | 4.32 | 12.20 | 12.40 | 10.01 ± 1.37 |
| 11 | 12.80 | 14.00 | 8.21 | 5.78 | 12.00 | 11.70 | 10.75 ± 1.27 |
| 12 | 12.90 | 12.20 | 8.81 | 5.24 | 10.70 | 10.20 | 10.01 ± 1.12 |
| 13 | 13.90 | 10.80 | 8.93 | 4.73 | 10.10 | 10.10 | 9.76 ± 1.22 |
| 14 | 15.00 | 10.80 | 10.10 | 4.04 | 10.10 | 9.94 | 10.00 ± 1.43 |
| 15 | 12.80 | 10.70 | 9.59 | 2.64 | 10.00 | 9.74 | 9.24 ± 1.41 |
| 16 | 12.80 | 10.20 | 8.70 | 0 | 9.84 | 8.83 | 8.40 ± 1.78 |
| 17 | 12.70 | 9.82 | 8.20 | 0 | 9.66 | 8.82 | 8.20 ± 1.76 |
| 18 | 12.00 | 9.65 | 8.11 | 0 | 9.10 | 8.81 | 7.95 ± 1.68 |
| 19 | 11.90 | 9.42 | 7.78 | 0 | 9.05 | 8.68 | 7.81 ± 1.66 |
| 20 | 11.30 | 9.35 | 7.74 | 0 | 9.01 | 8.03 | 7.57 ± 1.60 |
| 21 | 10.70 | 9.08 | 7.66 | 0 | 8.67 | 8.00 | 7.35 ± 1.53 |
| 22 | 10.10 | 9.04 | 7.31 | 0 | 8.60 | 7.92 | 7.16 ± 1.48 |
| 23 | 10.10 | 8.81 | 7.22 | 0 | 8.45 | 7.76 | 7.06 ± 1.47 |
| 24 | 9.65 | 8.68 | 6.80 | 0 | 8.16 | 7.72 | 6.84 ± 1.42 |

TABLE 4-continued

Area of Ischemic Lesions in MK-801
(0.1 mg/kg × 6, i.v.) MCAO Rats

Infarcted Area (mm²) of Each Test Animal

| Slice # | 1 | 2 | 3 | 4 | 5 | 6 | X ±SEM |
|---|---|---|---|---|---|---|---|
| BW (g) | 220 | 250 | 250 | 260 | 240 | 270 | N = 6 |
| 25 | 9.64 | 8.44 | 6.65 | 0 | 8.14 | 7.30 | 6.69 ± 1.40 |
| 26 | 8.88 | 8.01 | 5.95 | 0 | 7.66 | 6.87 | 6.23 ± 1.31 |
| 27 | 8.45 | 7.77 | 3.80 | 0 | 7.33 | 6.40 | 5.63 ± 1.30 |
| 28 | 8.44 | 7.68 | 3.47 | 0 | 7.17 | 6.00 | 5.46 ± 1.30 |
| 29 | 7.98 | 5.38 | 3.09 | 0 | 5.31 | 5.31 | 4.51 ± 1.10 |
| 30 | 3.89 | 5.02 | 3.03 | 0 | 4.08 | 2.94 | 3.16 ± 0.70 |
| Total mm² | 254.31 | 258.41 | 163.11 | 30.91 | 223.44 | 226.36 | 192.76 ± 35.23 |
| Total mm³ | 99.18 | 100.78 | 63.61 | 12.05 | 87.14 | 88.28 | 75.17 ± 13.74* |
| % Inh. | 9.77 | 8.32 | 42.13 | 89.04 | 20.72 | 19.69 | 31.61 ± 12.50 |

TABLE 5

Body Temperature (° C.) At 0 Minute Before (Pre)
And 15 Min After (Post) Compound Treatment

| | | | 0 Hour Dosage | | | 6 Hours Dosage | | |
|---|---|---|---|---|---|---|---|---|
| Treatment | Route | N | Pre | Post | Δ | Pre | Post | Δ |
| Vehicle | IV | 1 | 37.9 | 36.0 | −1.9 | 37.4 | 37.9 | 0.5 |
| (5 ml/kg) | IV | 2 | 38.1 | 36.8 | −1.3 | 37.6 | 38.4 | 0.8 |
| | IV | 3 | 37.9 | 36.5 | −1.4 | 37.3 | 38.0 | 0.7 |
| | IV | 4 | 38.4 | 37.8 | −0.6 | 38.1 | 36.4 | −1.7 |
| | IV | 5 | 38.1 | 38.7 | 0.6 | 37.3 | 38.0 | 0.7 |
| | IV | 6 | 37.5 | 36.1 | −1.4 | 37.9 | 37.8 | −0.1 |
| | X | | 38.0 | 37.0 | −1.0 | 37.6 | 37.8 | 0.1 |
| | SEM | | 0.1 | 0.4 | 0.4 | 0.1 | 0.3 | 0.4 |

| | | | 24 Hours Dosage | | | 30 Hours Dosage | | |
|---|---|---|---|---|---|---|---|---|
| Treatment | Route | N | Pre | Post | Δ | Pre | Post | Δ |
| Vehicle | IV | 1 | 38.3 | 38.0 | −0.3 | 37.7 | 37.2 | −0.5 |
| (5 ml/kg) | IV | 2 | 38.1 | 37.9 | −0.2 | 37.7 | 38.2 | 0.5 |
| | IV | 3 | 37.6 | 36.2 | −1.4 | 37.9 | 37.5 | −0.4 |
| | IV | 4 | 38.2 | 37.5 | −0.7 | 37.3 | 37.9 | 0.6 |
| | IV | 5 | 37.9 | 37.3 | −0.6 | 38.1 | 37.8 | −0.3 |
| | IV | 6 | 38.0 | 37.9 | −0.1 | 37.6 | 38.0 | 0.4 |
| | X | | 38.0 | 37.5 | −0.5 | 37.7 | 37.8 | 0.1 |
| | SEM | | 0.1 | 0.3 | 0.2 | 0.1 | 0.1 | 0.2 |

| | | | 48 Hours Dosage | | | 54 Hours Dosage | | |
|---|---|---|---|---|---|---|---|---|
| Treatment | Route | N | Pre | Post | Δ | Pre | Post | Δ |
| Vehicle | IV | 1 | 37.9 | 37.0 | −0.9 | 37.9 | 38.0 | 0.1 |
| (5 ml/kg) | IV | 2 | 38.0 | 37.5 | −0.5 | 37.6 | 37.9 | 0.3 |
| | IV | 3 | 37.4 | 38.0 | 0.6 | 38.2 | 38.1 | −0.1 |
| | IV | 4 | 37.3 | 38.5 | 1.2 | 38.7 | 39.0 | 0.3 |
| | IV | 5 | 37.1 | 37.7 | 0.6 | 38.5 | 38.3 | −0.2 |
| | IV | 6 | 37.6 | 37.5 | −0.1 | 37.7 | 38.0 | 0.3 |
| | X | | 37.6 | 37.7 | 0.2 | 38.1 | 38.2 | 0.1 |
| | SEM | | 0.1 | 0.2 | 0.3 | 0.2 | 0.2 | 0.1 |

TABLE 6

Body Temperature (° C.) At 0 Minute Before (Pre)
And 15 Min After (Post) Compound Treatment

| | | | 0 Hour Dosage | | | 6 Hours Dosage | | |
|---|---|---|---|---|---|---|---|---|
| Treatment | Route | N | Pre | Post | Δ | Pre | Post | Δ |
| PT #1010853-ADD | IV | 1 | 37.0 | 36.3 | −0.7 | 37.8 | 38.3 | 0.5 |
| (NTU-12) | IV | 2 | 38.0 | 37.1 | −0.9 | 37.9 | 38.5 | 0.6 |
| (NTU-106) | IV | 3 | 37.0 | 37.6 | 0.6 | 38.3 | 38.3 | 0 |
| (0.1 mg/kg × 6) | IV | 4 | 36.9 | 37.9 | 1.0 | 38.2 | 38.6 | 0.4 |
| | IV | 5 | 37.4 | 37.1 | −0.3 | 38.1 | 37.8 | −0.3 |
| | IV | 6 | 37.5 | 36.9 | −0.6 | 37.5 | 38.4 | 0.9 |
| | X | | 37.3 | 37.1 | −0.1 | 38.0 | 38.3 | 0.3 |
| | SEM | | 0.2 | 0.2 | 0.3 | 0.1 | 0.1 | 0.2 |

| | | | 24 Hours Dosage | | | 30 Hours Dosage | | |
|---|---|---|---|---|---|---|---|---|
| Treatment | Route | N | Pre | Post | Δ | Pre | Post | Δ |
| PT #1010853-ADD | IV | 1 | 37.6 | 36.8 | −0.8 | 38.5 | 37.9 | −0.6 |
| (NTU-12) | IV | 2 | 38.6 | 38.2 | −0.6 | 37.7 | 37.7 | 0 |
| (NTU-106) | IV | 3 | 38.1 | 37.9 | −0.2 | 37.9 | 38.3 | 0.4 |
| (0.1 mg/kg × 6) | IV | 4 | 38.0 | 37.8 | −0.2 | 38.9 | 38.4 | −0.5 |
| | IV | 5 | 38.0 | 37.7 | −0.3 | 38.3 | 38.0 | −0.3 |
| | IV | 6 | 37.8 | 38.0 | 0.2 | 38.0 | 37.9 | −0.1 |

TABLE 6-continued

Body Temperature (° C.) At 0 Minute Before (Pre)
And 15 Min After (Post) Compound Treatment

| | | | | | | | | |
|---|---|---|---|---|---|---|---|---|
| | X | | 38.0 | 37.7 | −0.3 | 38.2 | 38.1 | −0.2 |
| | SEM | | 0.1 | 0.2 | 0.1 | 0.2 | 0.1 | 0.1 |

| | | | 48 Hours Dosage | | | 54 Hours Dosage | | |
|---|---|---|---|---|---|---|---|---|
| Treatment | Route | N | Pre | Post | Δ | Pre | Post | Δ |
| PT #1010853-ADD | IV | 1 | 37.9 | 37.5 | −0.4 | 37.9 | 38.2 | 0.3 |
| (NTU-12) | IV | 2 | 38.2 | 38.0 | −0.2 | 37.5 | 38.0 | 0.5 |
| (NTU-106) | IV | 3 | 38.2 | 37.6 | −0.6 | 38.0 | 37.6 | −0.4 |
| (0.1 mg/kg × 6) | IV | 4 | 38.5 | 38.1 | −0.4 | 38.0 | 38.2 | 0.2 |
| | IV | 5 | 37.7 | 38.0 | 0.3 | 37.4 | 37.8 | 0.4 |
| | IV | 6 | 38.2 | 38.0 | −0.2 | 37.7 | 38.0 | 0.3 |
| | X | | 38.1 | 37.9 | −0.3 | 37.7 | 38.0 | 0.2 |
| | SEM | | 0.1 | 0.1 | 0.1 | 0.1 | 0.1 | 0.1 |

TABLE 7

Body Temperature (° C.) At 0 Minute Before (Pre)
And 15 Min After (Post) Compound Treatment

| | | | 0 Hour Dosage | | | 6 Hours Dosage | | |
|---|---|---|---|---|---|---|---|---|
| Treatment | Route | N | Pre | Post | Δ | Pre | Post | Δ |
| MK-801 | IV | 1 | 39.0 | 36.5 | −2.5 | 38.1 | 38.6 | 0.5 |
| (0.1 mg/kg × 6) | IV | 2 | 38.3 | 35.9 | −2.4 | 37.8 | 37.5 | −0.3 |
| | IV | 3 | 37.9 | 35.4 | −2.5 | 37.7 | 37.7 | 0 |
| | IV | 4 | 38.7 | 36.1 | −2.6 | 37.8 | 37.7 | −0.1 |
| | IV | 5 | 36.8 | 36.0 | −0.8 | 37.7 | 37.3 | −0.4 |
| | IV | 6 | 37.1 | 35.6 | −1.5 | 38.0 | 38.7 | 0.7 |
| | X | | 38.0 | 35.9 | −2.0 | 37.8 | 37.9 | 0.1 |
| | SEM | | 0.4 | 0.2 | 0.3 | 0.1 | 0.2 | 0.2 |

| | | | 24 Hours Dosage | | | 30 Hours Dosage | | |
|---|---|---|---|---|---|---|---|---|
| Treatment | Route | N | Pre | Post | Δ | Pre | Post | Δ |
| MK-801 | IV | 1 | 37.7 | 38.2 | 0.5 | 37.0 | 37.2 | 0.2 |
| (0.1 mg/kg × 6) | IV | 2 | 37.5 | 37.2 | 0.3 | 37.7 | 38.0 | 0.3 |
| | IV | 3 | 37.6 | 37.5 | −0.1 | 37.3 | 38.2 | 0.9 |
| | IV | 4 | 37.8 | 38.0 | 0.2 | 37.9 | 37.9 | 0 |
| | IV | 5 | 37.9 | 37.3 | −0.6 | 38.1 | 37.5 | −0.6 |
| | IV | 6 | 37.3 | 36.9 | −0.4 | 37.4 | 38.2 | 0.8 |
| | X | | 37.8 | 37.5 | 0 | 37.6 | 37.8 | 0.3 |
| | SEM | | 0.1 | 0.2 | 0.2 | 0.2 | 0.2 | 0.2 |

| | | | 48 Hours Dosage | | | 54 Hours Dosage | | |
|---|---|---|---|---|---|---|---|---|
| Treatment | Route | N | Pre | Post | Δ | Pre | Post | Δ |
| MK-801 | IV | 1 | 38.0 | 37.3 | −0.7 | 37.8 | 38.5 | 0.7 |
| (0.1 mg/kg × 6) | IV | 2 | 38.0 | 37.3 | −0.7 | 37.5 | 38.1 | 0.6 |
| | IV | 3 | 37.5 | 37.2 | −0.3 | 37.4 | 38.0 | 0.6 |
| | IV | 4 | 37.7 | 38.4 | 0.7 | 37.9 | 39.0 | 1.1 |
| | IV | 5 | 37.7 | 38.0 | 0.3 | 37.7 | 37.6 | −0.1 |
| | IV | 6 | 37.3 | 36.9 | −0.4 | 37.7 | 36.8 | −0.9 |
| | X | | 37.7 | 37.5 | −0.2 | 37.7 | 38.0 | 0.3 |
| | SEM | | 0.1 | 0.2 | 0.2 | 0.1 | 0.3 | 0.3 |

In above-mentioned specific formula VI compound (Liriodenine) for preventing or treating ischemic disease by maintaining or increasing eNOS, $R_1$, $R_2$, $R_3$, $R_4$ and $R_5$ are H.

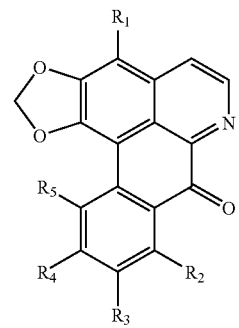

VI

In addition to Liriodenine, other aporphine and oxoaporphine compounds having the same activity may include formula VI compounds, where $R_1$ and $R_2$ are each selected from OH, O-acyl, OMe, F, Cl, Br, $NO_2$ and CN; $R_3$ and $R_4$ are each selected from OH, OEt, O"Pr, O'Pr and O-acyl; and $R_5$ is OH, O-acyl, or OMe. All these compounds can be used to prevent or treat ischemic diseases in human or other mammals.

Besides the above-mentioned formula VI aporphine and oxoaporphine compounds, other aporphine and oxoaporphine compounds for preventing or treating ischemic diseases in accordance with some embodiments of the invention may include formula I compounds:

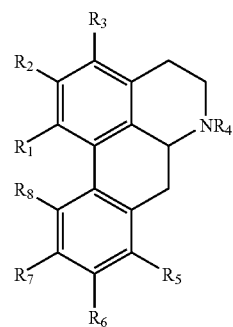

I where $R_1$, $R_2$, $R_6$, and $R_7$ are each selected from H, OH, O-acyl, OMe, OEt, O″Pr and O$^i$Pr; $R_3$ and $R_5$ are each selected from H, OH, O-acyl, OMe, F, Cl, Br, $NH_2$, $NO_2$ and CN; $R_4$ is allyl or $C_nH_{2n+1}$, $n \geq 0$; and $R_8$ is H, OH, or OMe.

The aporphine and oxoaporphine compounds for preventing or treating ischemic diseases in accordance with some embodiments of the invention may include formula II compounds:

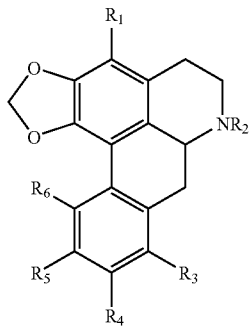

II where $R_1$ and $R_3$ are each selected from H, OH, O-acyl, OMe, F, Cl, Br, $NH_2$, $NO_2$ and CN; $R_2$ is allyl or $C_nH_{2n+1}$, $n \geq 0$, $R_4$; and $R_5$ is selected from H, OH, O-acyl, OMe, OEt, O″Pr, and O$^i$Pr; and $R_6$ is H, OH, O-acyl, or OMe.

The aporphine and oxoaporphine compounds for preventing or treating ischemic diseases in accordance with some embodiments of the invention may include formula III compounds:

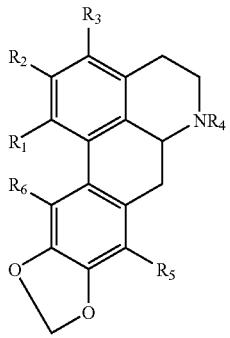

III where $R_1$ and $R_2$ are each selected from H, OH, O-acyl, OMe, OEt, O″Pr and O$^i$Pr; $R_3$ and $R_5$ are each selected from H, OH, O-acyl, OMe, Cl, Br, $NH_2$, $NO_2$ and CN; $R_4$ is allyl or $C_nH_{2n+1}$, $n \geq 0$; and $R_6$ is H, OH, O-acyl, or OMe.

The aporphine and oxoaporphine compounds for preventing or treating ischemic diseases in accordance with some embodiments of the invention may include formula IV compounds:

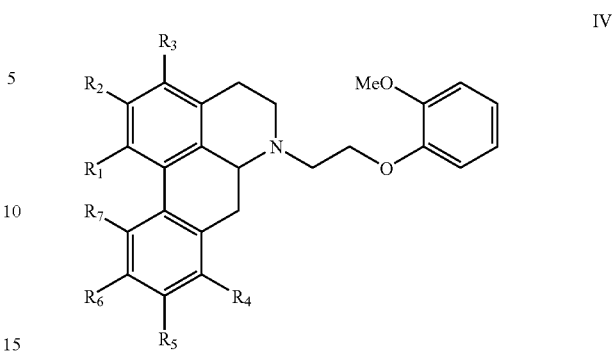

IV where $R_1$, $R_2$, $R_5$ and $R_6$ are each selected from H, OH, O-acyl, OMe, OEt, O″Pr, and O$^i$Pr; $R_3$ and $R_4$ are each selected from H, OH, O-acyl, OMe, F, Cl, Br, $NH_2$, $NO_2$ and CN; and $R_7$ is H, OH, O-acyl, or OMe.

The aporphine and oxoaporphine compounds for preventing or treating ischemic diseases in accordance with some embodiments of the invention may include formula V compounds:

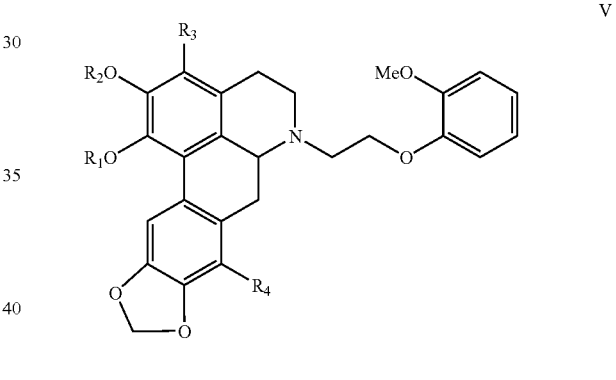

V where $R_1$ and $R_2$ are each selected from H, acyl, Me, Et, ″Pr and $^i$Pr; $R_3$ and $R_4$ are each selected from H, OH, O-acyl, OMe, F, Cl, Br, $NH_2$, $NO_2$ and CN.

The aporphine and oxoaporphine compounds for preventing or treating ischemic diseases in accordance with some embodiments of the invention may include formula VII compounds:

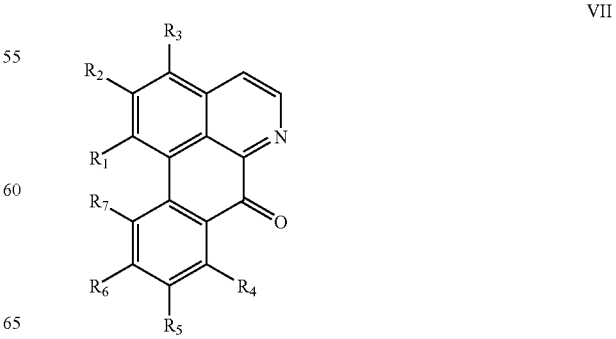

VII where $R_1$, $R_2$, $R_5$ and $R_6$ are each selected from H, OH, OAc, OMe, OEt, O''Pr and O'Pr; $R_3$ and $R_4$ are each selected from H, OH, O-acyl, OMe, F, Cl, Br, $NO_2$ and CN; $R_7$ is H, O-acyl, or OMe.

The aporphine and oxoaporphine compounds for preventing or treating ischemic diseases in accordance with some embodiments of the invention may include formula VIII compounds:

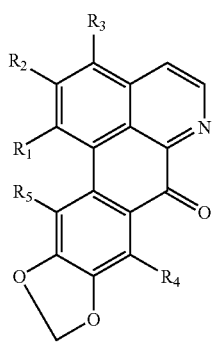

VIII where $R_1$ and $R_2$ are each selected from H, OH, O-acyl, OMe, OEt, O''Pr and O'Pr; $R_3$ and $R_4$ are each selected from H, OH, O-acyl, OMe, F, Cl, Br, $NO_2$ and CN; and $R_5$ is H, OH, O-acyl, or OMe.

Any of the above-mentioned formula I to VIII compounds can be used in combination or with a pharmaceutical acceptable carrier or excipient. Any carrier or excipient known in the art (e.g., lactose) may be used with embodiments of the invention.

All the aporphine and oxoaporphine compounds with different structures described above can be used to treat ischemic diseases in mammal or human being, and the ischemic diseases include ischemic cerebra apoplexy, ischemic cerebral thrombosis, ischemic cerebral embolism, hypoxic ischemic encephlopathy, ischemic cardiac disease, and ischemic enteropathy.

The above describes various aporphine and oxoaporphine compounds and their treatment effects. The following examples describe the preparations of the aporphine and oxoaporphine compounds in accordance with embodiments of the invention.

EXAMPLE 1

Preparation of 2,9-Diisopropyloxy-1,10-dimethoxy-7-oxoaporphine(3), the formula VII compound, wherein R1=R6=OMe, R2=R5=OiPr, R3=R4=R7=H; and 9-Hydroxy-2-isopropyloxy-1,10-dimethoxy-7-oxoaporphine(4), the formula VII compound, wherein R1=R6=OMe, R2=OiPr, R3=R4=R7=H, R5=OH.

1. Preparation of 2,9-Diisopropyloxy-1,10-dimethoxy-N-methylaporphine (2), the formula I compound, wherein $R_1$=$R_7$=OMe, $R_2$=$R_6$=O'Pr, $R_3$=$R_5$=$R_8$=H, $R_4$=Me.

The mixture of boldine (1) (1.63 g, 5 mmol), anhydrous alcohol (50 ml), and anhydrous potassium carbonate (3.0 g) in a 250 ml round bottom flask was stirred in an oil bath (70° C.). A solution of 2-iodopropane (3.4 g, 20 mmol) in anhydrous alcohol solution (10 ml) was added dropwise over 1 hour. The reaction was allowed to proceed for 8 hours and then the solution was cooled to room temperature. The inorganic sediments were filtered and washed with alcohol. The combined filtrate and washings were concentrated under reduced pressure. The residue obtained was dissolved in chloroform (150 ml), then extracted successively with 10% sodium hydroxide solution (50 ml) and water (50 ml×3) to remove the impurity. The chloroform layer is dried with anhydrous sodium sulfate and concentrated under reduced pressure to give a residue, which was purified on a basic alumina column, and eluted with chloroform to obtain 2,9-diisopropyloxy-1,10-dimethoxy-N-methylaporphine (2) (1.54 g, 75% yield): $^1$H NMR (200 MHz, $CDCl_3$) δ 1.40 (6H, d, J=6.1 Hz, 2×$CH_3$), 1.43 (6H, d, J=6.2 Hz, 2×$CH_3$), 2.52 (3H, s, $NCH_3$), 3.64 (3H, s, 1-$OCH_3$), 3.85 (3H, s, 10-$OCH_3$), 4.54 (1H, m) and 4.59 (1H, m) (2×OCH), 6.56 (1H, s, H-3), 6.76 (1H, s, H-8), 8.06 (1H, s, H-11).

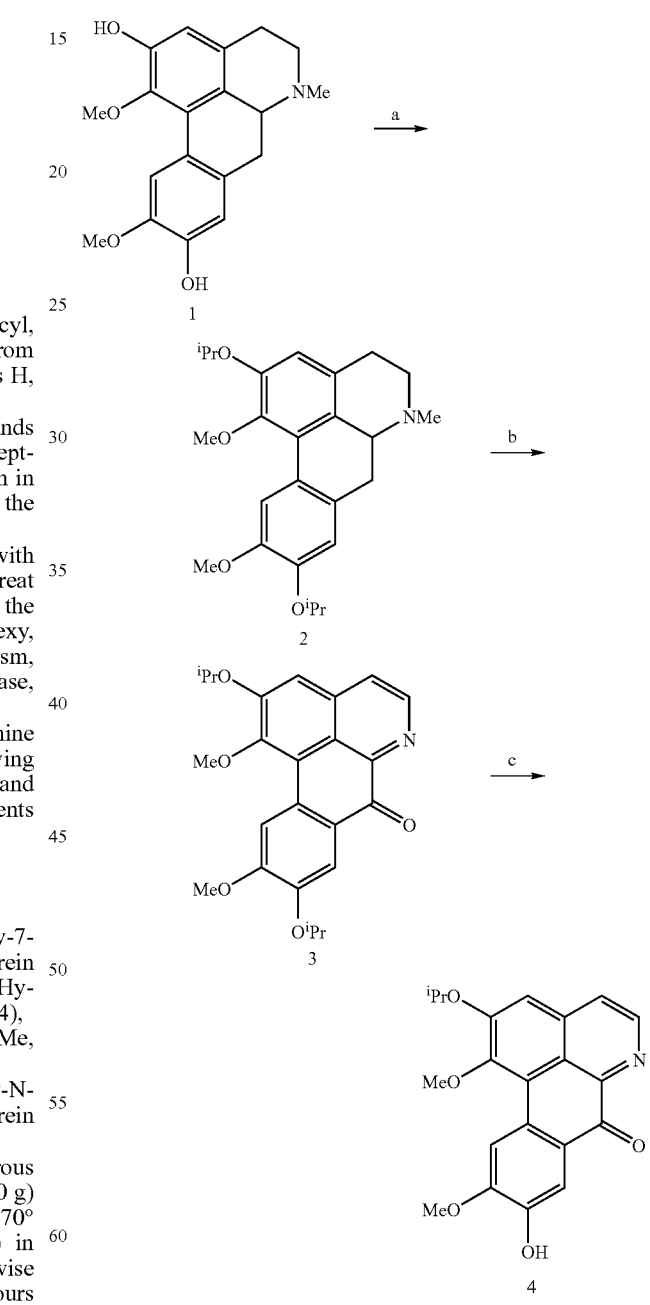

a. $^i$PrI/$K_2CO_3$, abs. EtOH, 70° C., 8 hr, 75%;
b; Pb(OAc)$_4$, HOAc, rt, 12 hr, 50%; c. 4%
$H_2SO_4$——HOAc, $N_2$, Δ, 1 hr, 22%.

2. Preparation of 2,9-diisopropyloxy-1,10-dimethoxy-7-oxoaporphine (3), a formula VII compound, wherein $R_1=R_6=OMe$, $R_2=R_5=O^iPr$, $R_3=R_4=R_7=H$.

To a solution of compound (2) (137 mg, 330 μM) in acetic acid (5 ml) was added lead tetraacetate (95%, 483 mg, 1.09 mmol). The reaction mixture was stirred for 12 hours at room temperature, then water (150 ml) was added, followed by successive extraction with chloroform (50 ml×4). The combined chloroform layers were washed successively with saturated sodium bicarbonate aqueous solution (50 ml), 10% sodium hyposulfite aqueous solution (50 ml) and water (50 ml×2), dried with anhydrous sodium sulfate, and concentrated under reduced pressure. The residue obtained was purified on a silica gel column and eluted with chloroform to give 2,9-diisopropyloxy-1,10-dimethoxy-7-oxoaporphine (3) (68 mg, 50% yield): m.p. 82–84° C.; IR(KBr)$v_{max}$ 2976, 2933, 1654, 1590, 1563, 1508, 1459, 1431, 1416, 1359, 1296, 1275, 1241, 1216, 1138, 1110, 1057, 1009, 995, 925, 887, 864, 782 cm$^-$; $^1$H NMR(200 MHz, CDCl$_3$) δ 1.44 (6H, d, J=6.1 Hz, 2×CH$_3$), 1.53 (6H, d, J=6.1 Hz, 2×CH$_3$), 4.01 (3H, s, 1-OCH$_3$), 3.85 (3H, s, 10-OCH$_3$), 4.87 (2H, m) (2×OCH), 7.79 (1H, d, J=5.4 Hz, H-4), 7.96 (1H, s, H-8), 8.75 (1H, s, H-11), 8.86 (1H, d, J=5.4 Hz, H-5); $^{13}$C NMR(50 MHz, CDCl$_3$) δ 21.7 (2C, q), 21.9 (2C, q), 56.0 (q), 60.4 (q), 70.9 (d), 71.2 (d), 107.2 (d), 110.6 (d), 112.2 (d), 120.2 (s), 121.3 (s), 123.2 (d), 126.7 (s), 128.8 (s), 135.4 (s), 145.9 (d), 145.3 (s), 147.8 (s), 151.5 (s), 154.6 (s), 154.8 (s), 181.3 (s); ESI MS (positive): [M+H]$^+$ 408.

3: Preparation of 9-hydroxy-2-isopropyloxy-1,10-dimethoxy-7-oxoaporphine (4), a formula II compound, wherein $R_1=R_6=OMe$, $R_2=R_5=O^iPr$, $R_3=R_4=R_7=H$.

The solution of compound (3) (50 mg) in acetic acid-sulfuric acid solution (96:4, 5 ml) was refluxed for 1 hour under nitrogen. After cooling to room temperature, the solution was evaporated under vacuum. The residue was neutralized with ammonia water and extracted with chloroform (100 ml ×2). The combined chloroform layers were washed with water (50 ml×2), dried over anhydrous sodium sulfate, concentrated under reduced pressure. The residue obtained was purified on a silica gel column and eluted with chloroform-methanol (99:3) to obtain a brown solid, 9-hydroxy-2-isopropyloxy-1,10-dimethoxy-7-oxoaporphine (4) (10 mg, 22% yield): m.p. 240–242° C.; IR(KBr) $v_{max}$ 3422, 3008, 2977, 2932, 1728, 1651, 1593, 1513, 1461, 1417, 1380, 1351, 1280, 1247, 1213, 1149, 1116, 1059, 1013, 932, 894, 866, 822 cm$^{-1}$; $^1$H NMR (200 MHz, CD$_3$OD) δ 1.51 (6H, d, J=6.0 Hz, 2×CH$_3$), 4.01 (3H, s, OCH$_3$), 4.02 (3H, s, OCH$_3$), 4.87 (1H, m, OCH), 7.25 (1H, s, H-3), 7.74 (1H, s, H-8), 7.83 (1H, d, J=4.8 Hz, H-4), 8.63 (1H, d, J=4.8 Hz, H-5), 8.68 (1H, s, H-11); ESI MS (positive): [M+H]$^+$ 366.

EXAMPLE 2

Preparation of 1,10-dimethoxy-7-oxoaporphine (7), a formula VII compound, wherein R1=R6=Me, R2=R3=R4=R5=R7=H.

1. Preparation of 1,10-dimethoxy-N-methylaporphine (6), a formula I compound, wherein R1=R7=OMe, R2=R3=R5=R6=R8=H, R4=Me.

Boldine [(1), 10.0 g, 30.58 mmol], actonitrile (350 ml), anhydrous potassium carbonate (8.4 g, 61 mmol) and 5-chloro-1-phenyltetrazole (TzCl, 12.14 g, 33.64 mmol) are placed in a 500-ml round bottom flask in sequence. The mixture was heated under reflux for 24 hours. After cooling to room temperature, the insoluble inorganic salts were removed by filtration, and the sediment was washed with acetonitrile. The filtrate and acetonitrile washings were concentrated under reduced pressure to give a residue, which was suspended in chloroform (400 ml) and then extracted with water (200 ml×2) to remove the impurity. The chloroform layer, after being dried with anhydrous sodium sulfate, was concentrated. The residue was purified on a silica gel column (500 g) and eluted with chloroform-methanol (99:1) to give 2,9-O-bis(1-phenyltetrazol-5-yl)-1,10-dimethoxy-N-methylaporphine (5) (18 g, 96% yield):$^1$H NMR (400 MHz, CDCl$_3$) δ 2.55 (3H, s, NCH$_3$), 3.46 (3H, s, 1-OCH$_3$), 3.76 (3H, s, 10-OCH$_3$), 7.19 (1H, s, H-3), 7.31 (1H, s, H-8), 7.42–7.60 (6H, m), and 7.83–7.87 (4H, m) (C$_6$H$_5$×2), 8.04 (1H, s, H-11).

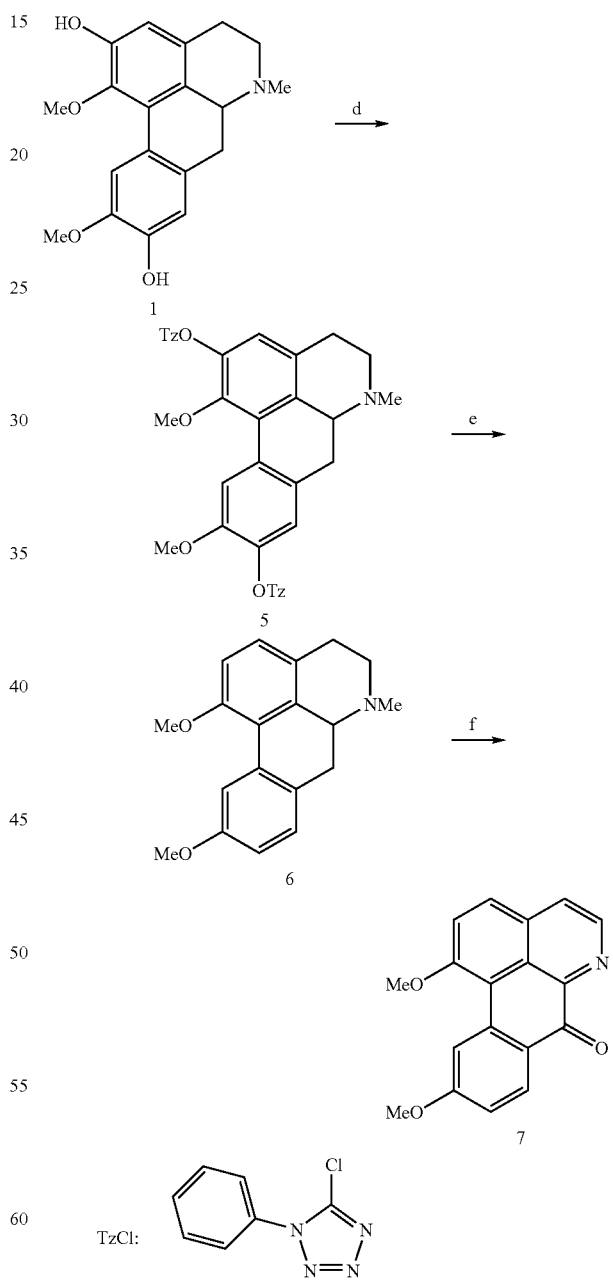

d. TzCl/K$_2$CO$_3$, MeCN, Δ, 24 hrs, 96%; e. 10% Pd—C, H$_2$ (120 psi), HOAc, 50° C., 3 d, 90%; f. Tl(OAc)$_3$, HOAc, 70° C., 1 hr, 69%.

To a solution of compound (5) (8 g) in acetic acid (55 ml) was added palladium carbon (10%, 1 g). The suspension was catalytically hydrogenated ($H_2$, 120 psi) at 50° C. for 3 days. After cooling, the reaction mixture was filtered through a Celite pad and the sediment was washed with chloroform. The combined filtrate and washing were concentrated under reduced pressure. The residue obtained was dissolved in chloroform (200 ml), extracted with 10% sodium hydroxide aqueous solution (50 ml×2) and water (100×2) to remove impurities. The chloroform layer, after being dried with anhydrous sodium sulfate, was concentrated under reduced pressure to give a residue, which was purified on a silica gel column and eluted with chloroform-methanol (98:2) to give 1,10-dimethoxy-N-methylaporphine (6) (4.12 g, 90% yield): $^1$H NMR(200 MHz, $CDCl_3$) δ 2.55 (3H, s, $NCH_3$), 3.82 (3H, s, 1-$OCH_3$), 3.85 (3H, s, 10-$OCH_3$), 6.76 (1H, dd, J=2.7, 8.3 Hz, H-9), 6.87 (1H, d, J=8.5 Hz, H-2), 7.04 (1H, d, J=8.5 Hz, H-3), 7.16 (1H, d, J=8.3 Hz, H-8), 7.89 (1H, d, J=2.7 Hz, H-11); $^{13}$C NMR(50 MHz, $CDCl_3$) δ 28.3 (t), 33.6 (t), 43.7 (q), 53.1 (t), 55.3 (q), 55.7 (q), 63.1 (d), 110.9 (d), 112.1 (d), 114.7 (d), 121.9 (s), 125.2 (s), 128.1 (d), 128.3 (s), 128.6 (d), 133.0 (s), 136.2 (s), 155.0 (s), 158.1 (s).

2. Preparation of 1,10-Dimethoxy-7-oxoaporphine (7), a formula VII compound, wherein $R_1$=$R_6$=Me, $R_2$=$R_3$=$R_4$=$R_5$=$R_7$=H.

To a solution of compound (6) (148 mg, 0.5 mmol) in acetic acid (10 ml) was added thallium triacetate (816 mg, 2 mmol). The reaction mixture was stirred at 70° C. for 1 hour and then water (150 ml) was added. The solution formed was extracted with chloroform (50ml×4). The combined chloroform layers were washed successively with saturated sodium bicarbonate aqueous solution (50 ml), 10% sodium hyposulfite aqueous solution (50 ml) and water (50 ml×2), followed by drying with anhydrous sodium sulfate and concentration under reduced pressure. The residue obtained was purified on a silica gel column and eluted with chloroform-methanol (99:1) to give 1,10-dimethoxy-7-oxoaporphine (7) (100 mg, 69% yield): m.p. 162–164° C.; IR(KBr) $v_{max}$ 2934, 2839, 1644, 1617, 1584, 1540, 1484, 1455, 1406, 1373, 1351, 1325, 1255, 1169, 1119, 1048, 1025, 985, 859, 810 $cm^{-1}$; $^1$H NMR (400 MHz, $CDCl_3$—$CD_3OD$, $δ_{CHCl3}$ 7.24) δ 3.79 (3H, s, 10-$OCH_3$), 4.04 (3H, s, 1-$OCH_3$), 6.88 (1H, dd, J=2.4, 8.8 Hz, H-9), 7.47 (1H, d, J=9.2 Hz, H-2), 7.73 (1H, d, J=4.7 Hz, H-4), 7.77 (1H, d, J=9.2 Hz, H-3), 8.29 (1H, d, J=8.8 Hz, H-8), 8.35 (1H, d, J=2.4 Hz, H-11), 8.64 (1H, d, J=4.7 Hz, H-5); $^{13}$C NMR (100 MHz, $CDCl_3$-$CD_3OD$, $δ_{CHCl3}$ 77.0) δ 55.2 (q), 56.3 (q), 112.3 (s), 113.5 (d), 113.8 (d), 119.7(d), 124.9 (d), 125.0 (s), 125.9 (s), 130.7 (d), 130.8 (d), 132.3 (s), 136.6 (s), 141.8 (d), 144.6 (s), 159.0 (s), 164.2 (s), 180.7 (s); ESI MS (positive): $[M+Na]^+$ 314.

The invention provides aporphine and oxoaporphine compounds for preventing or treating ischemic diseases by maintaining or enhancing the endothelial nitric oxide synthase (eNOS) activity. These compounds can thereby prevent or treat ischemic diseases by maintaining or improving eNOS action. There are no significant side effects to the patients during the treatment of the ischemic diseases with the compounds. Typical side effects may include, for example, memory loss, body temperature decrease etc. Thus, compounds of the invention produce excellent results. When compared with conventional methods in the art for opening up blood vessel by lysing the infarcted thrombus, compounds of the present invention have better therapeutic efficacies by loosening and dilating blood vessels.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An aporphine compound having the following structure IV:

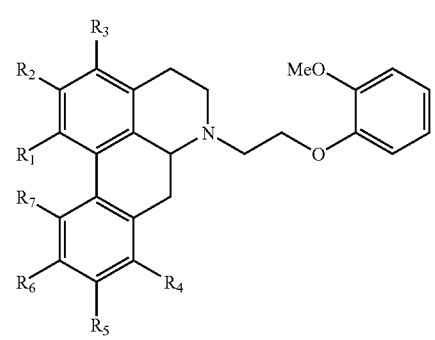

wherein $R_1$, $R_2$, $R_5$ and $R_6$ are each selected from H, OH, O-acyl, OMe, OEt, O″Pr and O$^i$Pr; $R_3$ and $R_4$ are each selected from H, OH, O-acyl, OMe, F, Cl, Br, $NH_2$, $NO_2$ and CN; and $R_7$ is selected from H, OH, O-acyl and OMe.

2. A pharmaceutical composition for treating an ischemic disease that is responsive to an expression level of epithelial nitric oxide synthase (eNOS), wherein the pharmaceutical composition comprises an effective amount of an aporphine compound having a structure shown as formula (IV) below and a pharmaceutically acceptable carrier or excipient,

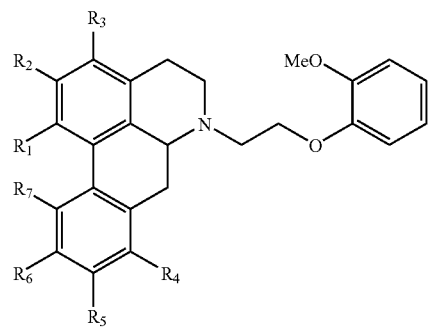

wherein $R_1$, $R_2$, $R_5$ and $R_6$ are each selected from H, OH, O-acyl, OMe, OEt, O″Pr and O$^i$Pr; $R_3$ and $R_4$ are each selected from H, OH, O-acyl, OMe, F, Cl, Br, $NH_2$, $NO_2$ and CN; and $R_7$ is selected from H, OH, O-acyl and OMe.

3. The pharmaceutical composition of claim 2, wherein the ischemic disease is one of ischemic stroke, ischemic cerebral apoplexy, ischemic cerebral thrombosis, ischemic cerebral embolism, hypoxic ischemic encephalopathy, ischemic cardiac disease, and ischemic enteropathy.

* * * * *